United States Patent [19]

Bisacchi et al.

[11] Patent Number: 4,751,245
[45] Date of Patent: Jun. 14, 1988

[54] ANTIFUNGAL DERIVATIVES OF N-(6,6-DIMETHYL-2-HEPTEN-4-YNYL)-1-NAPHTHALENEMETHANAMINE AND METHOD OF USING SAME

[75] Inventors: Gregory S. Bisacchi, Titusville; Robert Zahler, Princeton, both of N.J.

[73] Assignee: E. R. Squibb & Sons, Inc., Princeton, N.J.

[21] Appl. No.: 878,445

[22] Filed: Jun. 25, 1986

[51] Int. Cl.⁴ .................. A61K 31/135; A61K 31/205; C07C 87/28; C07C 123/00
[52] U.S. Cl. .................... 514/631; 260/501.1; 514/554; 514/645; 514/649; 564/300; 564/387; 568/448; 568/841; 568/842; 568/843; 568/873
[58] Field of Search ............... 514/645, 554, 631, 649; 260/501.1; 564/300, 228, 387

[56] References Cited

U.S. PATENT DOCUMENTS

| | | | |
|---|---|---|---|
| 3,184,510 | 5/1965 | Levy | 564/300 |
| 3,352,912 | 11/1967 | Prichard | 564/456 |
| 3,906,044 | 5/1975 | Aigami et al. | 564/225 |
| 4,087,460 | 5/1978 | Porter et al. | 564/300 |
| 4,143,073 | 3/1979 | Williams | 564/300 |
| 4,166,132 | 8/1979 | Kraska | 564/225 X |
| 4,282,251 | 8/1981 | Berney | 424/316 |
| 4,382,951 | 5/1983 | Grassberger et al. | 424/275 |

FOREIGN PATENT DOCUMENTS 0024587 3/1981 European Pat. Off. .

OTHER PUBLICATIONS

Stütz et al., "Synthesis and Structure-Activity Relationships of Naftifine-Related Allylamine Antimycotics", J. Med. Chem., 1986, 29, pp. 112–125.

Stütz et al., "Synthesis and Antifungal Activity of (E)-N-(6,6-Dimethyl-2-hepten-4-ynyl)-N-methyl-1-naphthalenemethanamine (SF 86–327) and Related Allylamine Derivatives with Enhanced Oral Activity", J. Med. Chem., 1984, 27, pp. 1539–1543.

Primary Examiner—Robert V. Hines
Attorney, Agent, or Firm—Lawrence S. Levinson; Theodore R. Furman, Jr.

[57] ABSTRACT

N-(6,6-dimethyl-2-hepten-4-ynyl)-1-naphthalenemethanamine derivatives are provided having the general formula

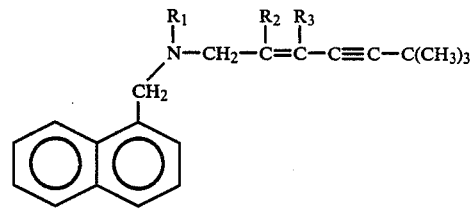

wherein $R_1$ is methoxy, iminomethyl or 1-iminoethyl and $R_2$ and $R_3$ are each hydrogen; or $R_1$ is methyl and one of $R_2$ and $R_3$ is hydrogen and the other is halogen.

The above compounds as well as acid-addition salts thereof are useful as antifungal agents.

15 Claims, No Drawings

ANTIFUNGAL DERIVATIVES OF N-(6,6-DIMETHYL-2-HEPTEN-4-YNYL)-1-NAPH-THALENEMETHANAMINE AND METHOD OF USING SAME

FIELD OF THE INVENTION

The present invention relates to new allylamine compounds and more particularly concerns allylamine derivatives useful as antifungal agents.

BACKGROUND OF THE INVENTION

A. Stütz, et al. (*J. Med. Chem.* 1984,27, p. 1539–1543) disclose new allylamine compounds. Specifically disclosed are (E)-N-(6,6-dimethyl-2-hepten-4-ynyl)-N-methyl-1-naphthalenemethanamine which has the formula

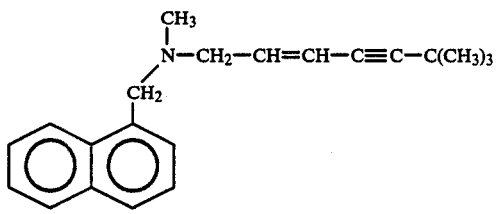

and related allylamine derivatives for use as antifungal agents. New compounds having antifungal activity would be a useful addition to the art.

SUMMARY OF THE INVENTION

In accordance with the present invention, new allylamine compounds having antifungal activity are provided. The new compounds of the present invention comprise N-(6,6-dimethyl-2-hepten-4-ynyl)-1-naphthalenemethanamine derivatives, including both Z and E isomers or mixtures thereof, and acid addition salts thereof. These new compounds have the general formula

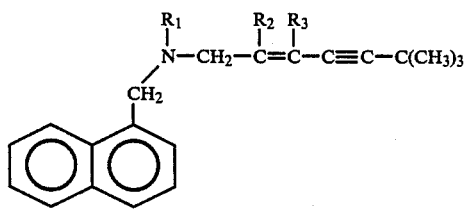

wherein $R_1$ is methoxy, iminomethyl or 1-iminoethyl and $R_2$ and $R_3$ are each hydrogen; or $R_1$ is methyl and one of $R_2$ and $R_3$ is hydrogen and the other is halogen.

Further, in accordance with the present invention, a method for using the compounds of formula I to treat fungal infections in mammals is described herein.

The term "halogen" refers to the four common halogens, fluorine, chlorine, bromine and iodine.

DETAILED DESCRIPTION OF THE INVENTION

Those compounds of formula I wherein $R_1$ is methoxy can be prepared by first alkylating methoxyamine hydrochloride with 1-chloromethylnaphthalene in an organic solvent, e.g. dimethylformamide, in the presence of a non-nucleophilic base, e.g. sodium carbonate. The resulting N-methoxy-1-naphthalenemethanamine can be alkylated with an allylic bromide of the formula

in an organic solvent, e.g. dimethylformamide, in the presence of a non-nucleophilic base, e.g. sodium carbonate, to yield the desired product of formula I wherein $R_1$ is methoxy.

Those compounds of formula I wherein $R_1$ is iminomethyl can be prepared by hydrolysis of the compound of formula II followed by oxidation. The resulting 6,6-dimethyl-2-hepten-4-ynal can be reacted with 1-naphthalenemethanamine in the presence of a hydride reducing agent, e.g. sodium cyanoborohydride, to obtain an allyl amine of the formula

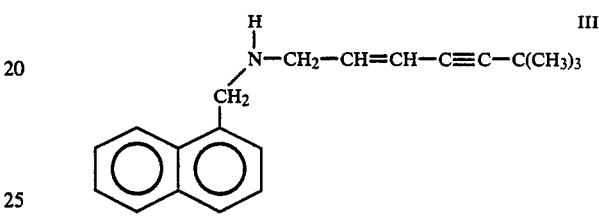

that is, N-(6,6-dimethyl-2-hepten-4-ynyl)-1-naphthalenemethanamine. Reaction of the amine of formula III with benzylformimidate hydrochloride in an organic solvent in the presence of a base produces the compound of formula I wherein $R_1$ is an iminomethyl group. Reaction of the amine of formula III with ethylacetimidate hydrochloride in an organic solvent in the presence of a base provides the compound of formula I wherein $R_1$ is a 1-iminoethyl group.

Those compounds of formula I wherein $R_1$ is methyl, $R_2$ is halogen and $R_3$ is hydrogen can be prepared by first reacting N-(6,6-dimethyl-2,4-heptadiynyl)-N-methyl-1-naphthalenemethanamine (the preparation of which has been disclosed by A. Stütz, et al. in *J. Med. Chem.*, 1984, 27, p 1539–43) with diisobutylaluminum hydride followed by quenching with an appropriate halogenating agent such as molecular iodine (for introduction of iodine), molecular bromine (for introduction of bromine), hexachloroethane (for introduction of chlorine), and perchloryl fluoride or N-fluoro-N-methyl-p-toluenesulfonamide (for introduction of fluorine).

Those compounds of formula I wherein $R_1$ is methyl, $R_2$ is hydrogen and $R_3$ is halogen can be obtained by first preparing 6,6-dimethyl-2,4-heptadiyn-1-ol having the formula

This intermediate compound can be made by a Cadiot-Chodkiewicz coupling of 1-bromo-2-t-butylacetylene with propargyl alcohol.

A reaction of the alcohol of formula IV with lithium aluminum hydride followed by quenching with one of the halogenating agents mentioned above affords an intermediate compound of the formula

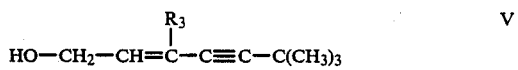

The hydroxyl group of the compound of formula V can be converted to a leaving group, L (e.g., methanesulfonate, p-toluenesufonate, chlorine, bromine or iodine), by methods known in the art to provide a compound of the formula

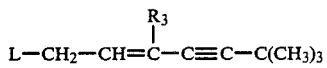

VI which is then reacted with N-methyl-1-naphthalenemethanamine in an organic solvent in the presence of a base to obtain the desired compound.

It will be appreciated that the compounds of formula I exist in the form of E and Z isomers. It is to be understood that the present invention embraces both isomeric forms and mixtures thereof. Isomeric mixtures can be separated, if so desired, into separate isomeric forms by known techniques. Conversely, single isomers can be converted to isomeric mixtures by irradiation with UV light, optionally in the presence of a sensitizer.

For example, the allylic bromide of formula II is known and can be obtained as a mixture of E and Z isomers. Since this compound of formula II is a common starting material leading to the compounds of formula I where $R_1$ is methoxy, iminomethyl or 1-iminoethyl, such formula I compounds can be produced as isomeric mixtures which can optionally be separated by known methods. Alternatively, an isomeric mixture of an intermediate compound derived from the allylic bromide of formula II can be separated and either isomer can be reacted to form the desired isomeric form of formula I.

Correspondingly, in the preparation of the compounds of formula I wherein $R_1$ is methyl, $R_2$ is hydrogen and $R_3$ is halogen, the intermediate compound of formula V can be made in each isomeric form (E or Z) or as mixtures thereof which can optionally be separated. For example, quenching of the lithium aluminum hydride reaction of the alcohol of formula IV with molecular iodine affords a mixture of E and Z isomers of the intermediate of formula V where $R_3$ is iodine. Quenching of the corresponding reaction of the alcohol of formula IV with hexachloroethane affords the Z isomer of the intermediate of formula V. Single isomers of the intermediate of formula V can be converted to isomeric mixtures by irradiation with UV light (optionally in the presence of a sensitizer). The particular isomer or mixture of isomers of the intermediate of formula V can then be converted to the corresponding isomer or mixture of isomers of the compounds of formula I where $R_1$ is methyl, $R_2$ is hydrogen and $R_3$ is halogen. Single isomers of the compounds of formula I where $R_1$ is methyl can be converted to isomeric mixtures by irradiation with UV light (optionally in the presence of a sensitizer). Isomeric mixtures of the compounds of formula I where $R_1$ is methyl can be optionally separated by known methods.

The compounds of formula I may be used in free base form or in the form of salts which are also embraced by the present invention. The salts include acid-addition salts, particularly the non-toxic, physiologically acceptable members. The bases of formula I form salts by reactions with one or more equivalents of any of a variety of the common inorganic and organic acids providing acid-addition salts including for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfonate and toluenesulfonate.

The new compounds of formula I and their salts are useful as anti-fungal agents and may be used to combat fungal infections in various mammalian species, such as humans and domesticated animals, particularly those due to organisms such as *Candida albicans*, as well as organisms such as *Trichomonas vaginalis* or *Trichophyton mentagrophytes*. For example, a compound or mixture of compounds of formula I or a physiologically acceptable acid-addition salt thereof can be administered orally to an infected mammalian host (e.g., humans and domesticated animals), in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc , as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following Examples are specific embodiments of the invention.

EXAMPLE 1

(Z)-N-(6,6-Dimethyl-2-hepten-4-ynyl)-N-methoxy1-naphthalenemethanamine (A)
N-Methoxy-1-naphthalenemethanamine 1-Chloromethylnaphthalene (1.85 g, 10 mmol) in 4 ml dimethylformamide (hereinafter DMF) was added dropwise to a mixture of methoxyamine hydrochloride (9.19 g, 110 mmol) and sodium carbonate (11.66 g, 110 mmol) in 100 ml of DMF at 0°–5° C. After stirring 20 minutes, the reaction was warmed to room temperature. After about 18 hours, the reaction was concentrated in vacuo and partitioned between ethyl ether and water. The aqueous layer was extracted twice with ethyl ether. Combined ethereal layers were washed once with water, twice with brine, dried over sodium sulfate and concentrated to 1.19 g of crude product which was further purified by bulb-to-bulb distillation (148°–168° C. at 0.7 mm of Hg), affording 0.947 g of N-methoxy-1-naphthalenemethanamine.

(B) E/Z Mixture of
N-(6,6-dimethyl-2-hepten-4-ynyl)-N-methoxy-1-naphthalenemethanamine To a stirred mixture of N-methoxy-1-naphthalenemethanamine (0.476 g, 2.54 mmol) and sodium carbonate (0.269 g, 2.54 mmol) in 2.5 ml DMF at 5° C. was added 1-bromo-6,6-dimethyl-2-hepten-4-yne (0.494 g, 2.45 mmol). The mixture was warmed to room temperature. After 20 hours, starting amine was still evident, so the mixture was warmed at 40° C. for 4.5 hours, then concentrated to a small volume and partitioned between ether and water. The ether phase was washed twice with 2% tartaric acid, then saturated aqueous sodium bicarbonate, dried over sodium sulfate and concentrated to afford 542 mg of crude product. This was filtered through a plug of silica gel eluting with toluene/ethyl acetate (4:1), then ethylacetate. After concentration, the crude product was chromatographed on silica gel (elution with hexane to 2% ether/hexane step-wise gradient) to afford the desired coupled product N-(6,6-dimethyl-2-hepten-4-ynyl)-N-methoxy-1-naphthalenemethanamine as a mixture of the E and Z isomers.

(C) (Z)-N-(6,6-Dimethyl-2-hepten-4-ynyl)-N-methoxy-1-naphthalenemethanamine

The E/Z mixture of N-(6,6-dimethyl-2-hepten-4-ynyl)-N-methoxy-1-naphthalenemethanamine was chromatographed on silica gel eluting with 1% ether/hexane. Appropriate fractions were pooled and concentrated to afford 88.3 mg of (Z)-N-(6,6-dimethyl2-hepten-4-ynyl)-N-methoxy-1-naphthalenemethanamine (containing about 12% of the E-amine) as a waxy solid.

EXAMPLE 2

(E)-N-(6,6-Dimethyl-2-hepten-4-ynyl)-N-methoxy-1-naphthalenemethanamine.

Appropriate fractions from step C of Example 1 were pooled and concentrated to afford 275.4 mg of (E)-N-(6,6-dimethyl-2-hepten-4-ynyl)-N-methoxy-1-naphthalenemethanamine (containing about 13% of the corresponding Z isomer) as a viscous oil.

EXAMPLE 3

(E)-N-(6,6-Dimethyl-2-hepten-4-ynyl)-N-(iminomethyl)-1-naphthalenemethanamine, monohydrochloride

(A) 6,6-Dimethyl-2-hepten-4-yn-1-ol

To 5.24 g (26.0 mmol) of an approximately 3:1 mixture of the E and Z isomers of 1-bromo-6,6-dimethyl-2-hepten-4-yne was added sodium carbonate (5.52 g, 52.0 mmol) 80 ml of acetone and 170 ml of water. This mixture was heated to reflux for 3 hours. After cooling, most of the acetone was removed in vacuo and the mixture was extracted with ethyl ether three times. The combined ether layer was dried with sodium sulfate and concentrated to afford 3.97 of 6,6-dimethyl-2-hepten-4-yn-1-ol.

(B) 6,6-Dimethyl-2-hepten-4-ynal

To 6,6-dimethyl-2-hepten-4-yn-1-ol (3.56 g, 25.8S mmol) dissolved in 100 ml of freshly distilled methylene chloride was added manganese dioxide (37 g, 425 mmol) and the mixture was stirred for 17 hours. An additional 5.2 g of manganese dioxide was then added and the mixture was stirred for 2 hours, then filtered and washed copiously with methylene chloride. Evaporation of the solvent afforded 2.74 g of 6,6-dimethyl-2-hepten-4-ynal.

(C) (E)-N-(6,6-Dimethyl-2-hepten-4-ynyl)-1-naphthalenemethanamine

A mixture of 1-naphthalenemethanamine (1.34 g, 8.51 mmol) and 6,6-dimethyl-2-hepten-4-ynal (1.16 g, 8.51 mmol) in 20 ml of dry ethyl ether was stirred over 4A sieves overnight. Sieve material was then removed by centrifugation, washed once with ethyl ether and the combined ether fractions concentrated to afford the crude condensed product. About 8.08 mmol of this material was stirred with sodium borohydride (343 mg, 9.06 mmol) in 20 ml of methanol at room temperature for 3.75 hours. The reaction mixture was partitioned between aqueous sodium bicarbonate and methylene chloride, the aqueous layer extracted twice with methylene chloride, and the combined organic solution washed with water and dried over magnesium sulfate. Removal of the solvent afforded N-(6,6-dimethyl-2-hepten-4-ynyl)-1-naphthalenemethanamine as a mixture of the E and Z isomers. Flash chromatography of this product on silica gel (5 cm column, eluting with 0.2% triethylamine in chloroform) afforded 0.74 g of the pure (E)-N-6,6-dimethyl-2-hepten-4-ynyl)-1-naphthalenemethanamine.

(D) (E)-N-(6,6-Dimethyl-2-hepten-4-ynyl)-N-(iminomethyl)-1-naphthalenemethanamine, monohydrochloride A mixture of (E)-N-(6,6-dimethyl-2-hepten-4-ynyl)-1-naphthalenemethanamine (21.1 mg, 76.1 μmol), diisopropylethylamine (60 μl, 350 μmol), benzyl formimidate hydrochloride (26 mg, 165 μmol), and catalytic DMAP in 2 ml of DMF at room temperature was stirred for 18 hours under nitrogen. An additional 26 mg of formimidate and 60 μl of base was added and stirring continued for 7 hours. Then the mixture was concentrated to dryness and the residue partitioned between water and methylene chloride. The methylene chloride layer was washed once with water, dried over magnesium sulfate and concentrated. The above reaction and work-up was then repeated on a larger scale (0.529 mmol of amine, 2.70 mmol of formimidate, 5.29 mmol diisopropylethylamine) and the crude products of both reactions combined. This combined crude product was twice flash chromatographed silica gel eluting with a step-wise gradient of methylenechloride-methanol. The desired product eluted from 15 to 20% methanol. Concentration of the appropriate fractions afforded 29 mg of (E)-N-(6,6-dimethyl-2-hepten-4-ynyl)-N-(iminomethyl)-1-naphthalenemethanamine, monohydrochloride as a glassy solid.

EXAMPLE 4

(E)-N-(6,6-Dimethyl-2-hepten-4-ynyl)-N-(1-iminoethyl)-1-naphthalenemethanamine, monohydrochloride A mixture of (E)-N-(6,6-dimethyl-2-hepten-4-ynyl)-1-naphthalenemethanamine (108 mg, 0.309 mmol) (as prepared in example 3, step C), diisopropylethylamine (503 mg, 3.89 mmol), and ethylacetimidate hydrochloride (242 mg, 1.96 mmol) in 1 ml of dry dimethoxyethane was heated for 3 hours at 106° C. during which time the solution separated into two layers. The upper phase was separated, mixed with additional diisopropylethylamine (3.89 mmol) and ethylacetimidate hydrochloride (1.96 mmol) and heated at 106° C. for 3 hours. Again the solution separated into two layers. The lower phases from the two runs were combined, diluted with ethyl acetate and washed twice with aqueous hydrochloric acid (pH ~1). The aqueous washes were back-extracted once with ethyl acetate. The combined ethyl acetate layers were dried with sodium sulfate and concentrated in vacuo to afford 93 mg of crude material. The crude product was purified by preparative TLC on silica gel eluting with chloroform-methanol 4:1, to afford 44 mg of the desired product as a light yellow solid.

EXAMPLE 5

(Z)-N-(3-Chloro-6,6-dimethyl-2-hepten-4-ynyl)-N-methyl-1-naphthalenemethanamine

(A) 6,6-Dimethyl-2,4-heptadiyne-1-ol

Nitrogen was bubbled through a mixture of cupric chloride (154 mg), NH$_2$OH.HCl (0.45 g), and 70% aqueous diethylamine (9 ml) in 11 ml of water and 23 ml of methanol, for a few minutes. Propargyl alcohol (3.8 g, 0.068 mol) was added with stirring under nitrogen whereupon a yellow precipitate formed immediately. The mixture was warmed to 35°–40° C. for 15 minutes and 1-bromo-2-t-butyl-acetylene (8.57 g, 0.053 mmol) was added over 15 minutes. The mixture was stirred at 35°–40° C. for 45 minutes, then at room temperature for 1 hour. Aqueous potassium cyanide (0.45 g in 45 ml of water) was added and the mixture was stirred for one minute. The mixture was poured into 50 ml of water and extracted 5 times with ether. The combined organic phase was washed with water and dried over magnesium sulfate. The solvents were removed and the residue was distilled under reduced pressure through a column packed with glass helices. 6,6-Dimethyl-2,4-heptadiyne-1-ol (3.63 grams) was collected at 85° C. and 0.5 mm of mercury.

(B) 3-Chloro-6,6-dimethyl-2-hepten-4-yn-1-ol

A solution of lithium aluminum hydride (11.4 mmol; 1M solution in tetrahydrofuran, (hereafter THF) was added to a stirred suspension of sodium methoxide (1.23 g, 22.8 mmol) in 18 ml of dry THF and the mixture was stirred at room temperature for ½ hour. 6,6-Dimethyl-2,4-heptadiyn-1-ol (777 mg, 5.71 mmol) was added and the mixture stirred at room temperature overnight. The mixture was cooled to 0° C. and dry ethyl acetate (1.0 g, 11.4 mmole) was added dropwise. Hexachloroethane (4.05 g, 17.13 mmole) was then added and the mixture was allowed to warm to room temperature. After 4.5 hours, additional hexachloroethane (1.35 g, 5.71 mmol) was added to the reaction mixture which was then stirred for 68 hours. The mixture was partitioned between ether and dilute aqueous hydrochloric acid, and the aqueous layer was extracted 3 times with ether. The combined ethereal extract was washed with water an brine, dried over anhydrous sodium sulfate and concentrated in vacuo to afford 3.43 g of crude product. This mixture was purified by chromatography on a column (2.5×47 cm) of silica gel eluting with ethyl acetate-hexane, 5/95. Combination and concentration of the appropriate fractions afforded 404 mg of the desired (Z)-3-chloro-6,6-dimethyl- 2-hepten-4-yn-1-ol.

(C)
(Z)-N-(3-Chloro-6,6-dimethyl-2-hepten-4-ynyl)-N-methyl-1-naphthalenemethanamine Methanesulfonyl chloride (106 mg, 0.924 mmole), was added dropwise to a stirred solution of (Z)-3-chloro-6,6-dimethyl-2-hepten-4-yn-1-ol (145 mg, 0.840 mmole) and triethylamine (127 mg, 1.26 mmol) in 10 ml of dry methylene chloride at −15° C. under nitrogen.

The mixture was stirred 40 minutes at −15° C. to −5° C., then was cooled to −78° C. and poured onto ice water. The organic phase was separated and washed with cold (0° C.) solutions of hydrochloric acid saturated sodium carbonate, and brine, and was dried over anhydrous sodium sulfate and concentrated in vacuo to afford the mesylate. To the mesylate, cooled to 0° C., was added with stirring a 0° C. solution of 152.2 mg (0.889 mmole) of N-methyl-1-naphthalenemethanamine in 10 ml of dry DMF. Sodium carbonate (102 mg, 0.962 mmole) was added and the mixture stirred at room temperature overnight. The DMF was removed in vacuo and the residue was partitioned between ether and water. The aqueous phase was extracted with ether and the combined ether solution was washed with water and brine, and dried over anhydrous sodium sulfate and concentrated in vacuo. The residue was purified on a column (1.5×27 cm) of silica gel eluting with ether-hexane 2:98. The chromatography and subsequent manipulations were conducted as much as. possible in the absence of light. Combination and concentration of the appropriate fractions afforded 157 mg of (Z)-N-(3-chloro-6,6-dimethyl-2-hepten-4-ynyl)- N-methyl-1-naphthalenemethanamine as a clear oil.

EXAMPLE 6

(E)-N-(3-Iodo-6,6-dimethyl-2-hepten-4-ynyl)-N-methyl-1-naphthalenemethanamine (A) 3-Iodo-6,6-dimethyl-2-hepten-4-yn-1-ol Lithium aluminum hydride (11.76 ml, 11.76 mmol; 1M solution in THF) was added to a stirred suspension of sodium methoxide (1.27 g, 23.5 mmol) in 20 ml of dry THF and the mixture was stirred for 0.5 hours at room temperature. 6,6-Dimethyl-2,4-heptadiyne-1-ol (808 mg, 5.93 mmol) as prepared in Example 5 was added dropwise as a solution in 2 ml of dry THF and the reaction was stirred at room temperature overnight. The mixture was cooled to 0° C. and dry ethyl acetate (1.15 ml, 11.76 mmol) was added slowly. The mixture was then cooled to −78° C. and a solution of iodine (7.46 g, 29.4 mmol) in dry THF was added. After a few minutes, the mixture was allowed to warm to room temperature and was poured into aqueous sodium thiosulfate (about 1 g in 100 ml water). The mixture was extracted 9X with ether and the combined organic phase was washed with water and brine, dried over anhydrous sodium sulfate, and concentrated in vacuo to afford 1.37 g of crude product. The crude was purified by column chromatography (2.5×48 cm) on silica gel eluting with ether-hexane 10/90. Concentration of the appropriate fractions afforded 3-iodo-6,6-dimethyl-2-hepten-4-yn-1-ol, 931 mg (mixture of E and Z isomers, about 3:2).

(B)
(E)-N-(3-Iodo-6,6-dimethyl-2-hepten-4-ynyl)-N-methyl-1-naphthalenemethanamine Methanesulfonyl chloride (160 mg, 1.39 mmol) was added dropwise to a stirred solution comprising 3-iodo-6,6-dimethyl-2-hepten-4-yn-1-ol (335 mg, 1.27 mmol) and triethylamine (193 mg, 1.90 mmol) in 10 ml of dry methylene chloride at −5° C. The solution was stirred at this temperature for 25 minutes, then cooled to −78° C. and poured into ice water. The organic phase was separated and washed with 0° C. solutions of 1N hydrochloric acid, saturated sodium bicarbonate and brine, then dried with sodium sulfate and concentrated to afford the mesylate as a yellow oil. To the mesylate cooled to 0° C. was added with stirring a 0° C. solution of N-methyl-naphthalenemethanamine (234 mg, 1.37 mmol) in 10 ml of dry DMF. Sodium carbonate (145 mg, 1.37 mmol) was added and the mixture was stirred overnight. Most of the DMF was removed in vacuo and the viscous residue was partitioned between ether and water. The aqueous phase was extracted twice with ether, the combined ether solution was washed with water and brine, dried over sodium sulfate and concentrated in vacuo to afford 454 mg of crude N-(3-iodo-6,6-dimethyl-2-hepten-4-ynyl)-N-methyl-1-naphthalenemethanamine as an E/Z isomeric mixture. This product was chromatographed in a column of silica gel eluting with ether:hexane 2:98 in the dark. Combination and concentration of the appropriate fractions afforded 208 mg of (E)-N-(3-iodo-6,6-dimethyl-2-hepten-4-ynyl)-N-methyl-1-naphthalenemethanamine, as well as 174 mg of the Z isomer and 38 mg of a mixture of the E and Z isomers.

What is claimed is:

1. A compound of the formula

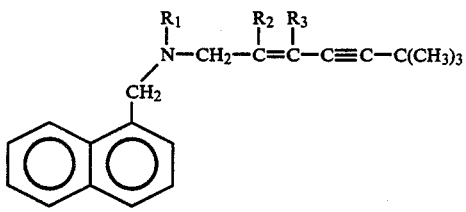

or a physiologically acceptable salt thereof, and including both the E and Z isomeric forms thereof, wherein $R_1$ is iminomethyl, or 1-iminoethyl, and $R_2$ and $R_3$ are each hydrogen; or wherein $R_1$ is methyl and one of $R_2$ and $R_3$ is hydrogen and the other is halogen.

2. A compound of claim 1 being a mixture of the E and Z isomeric forms.

3. A compound of claim 1 wherein $R_1$ is iminomethyl and $R_2$ and $R_3$ are each hydrogen.

4. A compound of claim 1 wherein $R_1$ is 1-iminoethyl and $R_2$ and $R_3$ are each hydrogen.

5. A compound of claim 1 wherein $R_1$ is methyl, $R_2$ is hydrogen and $R_3$ is halogen.

6. A compound of claim 1 wherein $R_1$ is methyl, $R_2$ is halogen and $R_3$ is hydrogen.

7. The compound of claim 1 having the name (E)-N-(6,6-dimethyl-2-hepten-4-ynyl)-N-(iminomethyl)-1-naphthalenemethanamine.

8. The compound of claim 7 in the form of its monohydrochloride salt.

9. The compound of claim 1 having the name (E)-N-(6,6-dimethyl-2-hepten-4-ynyl)-N-(1-iminoethyl)-1-naphthalenemethanamine.

10. The compound of claim 9 in the form of its monohydrochloride salt.

11. The compound of claim 1 having the name (Z)-N-(3-chloro-6,6-dimethyl-2-hepten-4-ynyl)-N-methyl-1-naphthalenemethanamine.

12. An antifungal composition comprising a compound of the formula

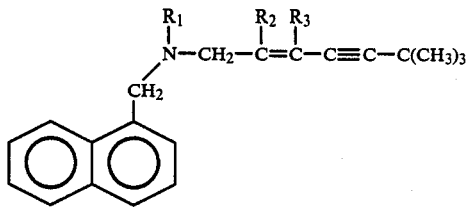

or a physiologically acceptable salt thereof, and including both the E and Z isomeric forms thereof, wherein $R_1$ is iminomethyl or 1-iminoethyl and $R_2$ and $R_3$ are each hydrogen; or wherein $R_1$ is methyl and one of $R_2$ and $R_3$ is hydrogen and the other is halogen.

13. A composition of claim 12 wherein said compound is a mixture of the E and Z isomeric forms.

14. A method for treating fungal infections in mammals which comprises administering to a mammalian host in need thereof an effective amount of a compound of the formula

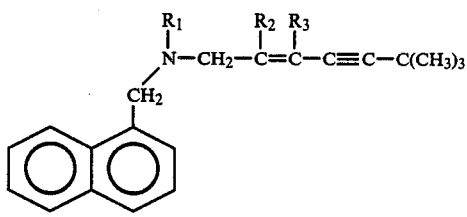

or a physiologically acceptable salt thereof, and including both the E and Z isomeric forms thereof, wherein $R_1$ is iminomethyl or 1-iminoethyl and $R_2$ and $R_3$ are each hydrogen; or wherein $R_1$ is methyl and one of $R_2$ and $R_3$ is hydrogen and the other is halogen.

15. A method in accordance with claim 11 wherein said compound is a mixture of the E and Z isomeric forms.

* * * * *